United States Patent [19]

Walloch

[11] Patent Number: 4,974,597
[45] Date of Patent: Dec. 4, 1990

[54] APPARATUS FOR IDENTIFYING ARTIFACT IN AUTOMATIC BLOOD PRESSURE MEASUREMENTS

[75] Inventor: Richard A. Walloch, Beaverton, Oreg.

[73] Assignee: SpaceLabs, Inc., Redmond, Wash.

[21] Appl. No.: 254,371

[22] Filed: Oct. 5, 1988

[51] Int. Cl.⁵ .............................................. A61B 5/02
[52] U.S. Cl. .................................... 128/680; 128/700
[58] Field of Search ................ 128/680, 681, 682, 700

[56] References Cited

U.S. PATENT DOCUMENTS 4,484,584 11/1984 Uemura ................................. 128/681
4,677,984 7/1987 Sramek ................................. 128/681
4,860,759 8/1989 Kahn et al. ........................... 128/700

Primary Examiner—Lee S. Cohen
Assistant Examiner—Kevin Pontius
Attorney, Agent, or Firm—Seed and Berry

[57] ABSTRACT

A system for identifying artifact in automatic blood pressure measuring system. The system determines whether a single blood pressure signal, such as an oscillometric pulse or Korotkoff sound, occurs for each QRS complex of an ECG waveform in order to verify that the blood pressure signal is valid. In the event that multiple blood pressure signals occur between successive QRS complexes, at least some of the blood pressure signals are determined to be induced by artifact.

5 Claims, 5 Drawing Sheets

APPARATUS FOR IDENTIFYING ARTIFACT IN AUTOMATIC BLOOD PRESSURE MEASUREMENTS

DESCRIPTION

1. Field of the Invention

This invention relates to the automatic measurement of blood pressure and, more particularly, to identifying false blood pressure signals induced by artifact.

2. Background Art

Automatic blood pressure systems are commonly used to periodically measure the blood pressure of a patient. In most automatic blood pressure measuring systems, a pressure cuff is attached to a patient's arm adjacent a blood vessel. The cuff is periodically pressurized with an applied pressure that is high enough to occlude the blood vessel. The cuff pressure is then gradually reduced, either continuously or in increments. As the pressure is reduced to systolic pressure, blood begins to flow through the blood vessel beneath the cuff.

As blood begins to flow through the blood vessel beneath the cuff, it produces Korotkoff sounds that are conventionally detected by either a stethoscope or an electronic microphone. In automatic measurement techniques, a microphone is used as a sensor which applies the signals corresponding to the Korotkoff sounds to a measurement unit. The measurement unit generally includes a processor programmed with software that is capable of determining whether the signal generated by the microphone has the characteristics of a Korotkoff sound. As a result, the systems are capable of determining whether the signals are truly indicative of a patient's blood pressure or whether they are induced by artifact, such as patient movement.

In addition, to utilizing Korotkoff sounds to determine a patient's blood pressure, automatic blood pressure measuring systems can also use oscillometric pulses to inidcate a patient's blood presure. Oscillometric pulses are minute changes in cuff pressure as a blood pressure wave moves through blood vessels beneath the cuff following each contraction of the heart. Like Korotkoff sounds, oscillometric peaks are used to obtain a clinical measure of a patient's blood pressure. Some conventional automatic blood pressure measuring systems measure the amplitude of the oscillometric pulses at each cuff pressure. Systole and diastole have been imperically defined as a function of the amplitudes of these oscillometric pulses.

As mentioned above, the Korotkoff sounds and oscillometric pulses are produced by contraction of the heart. As a result, there is normally a single Korotkoff sound and a single oscillometric pulse for each contraction of the heart. The electrical activity leading to a contraction is conventionally detected by placing electrodes on the patient and connecting the electrodes to an ECG monitor. The ECG signal veiwable on the monitor includes several well-defined waveforms known as the P, Q, R, S and T waves. Of these waves, the most prominent are the Q, R and S waves which together form a "QRS complex" that forms a very conspicuous portion of the ECG waveform. As a result, the QRS complex can be used to identify electrical activity in the heart.

Regardless of whether automatic blood pressure measurements are made using Korotkoff sounds or oscillometric pulses, blood pressure measurements are hindered by artifact, generally produced by patient movement. Motion artifact-induced pulses are difficult to distinguish from true oscillometric pulses. Similarly, motion-induced pulses can produce sounds that are picked up by the microphone of automatic blood pressure measuring systems detecting Korotkoff sounds. As a result, these motion artifact-induced sounds can be mistaken for Korotkoff sounds.

It is therefore possible for the automatic measurement unit to mistake motion artifact for oscillometric pulses or Korotkoff sounds thereby obtaining false blood pressure measurements. These false blood pressure measurements can prevent the automatic measurement unit from indicating the proper blood pressure and, in some cases, result in an improper diagnosis of a patient's condition.

DISCLOSURE OF THE INVENTION

It is an object of the invention to provide a method and apparatus for making blood pressure measurements using oscillometric pulses of Korotkoff sounds in a reliable manner despite the possible presence of motion artifact.

It is another object of the invention to provide a method and apparatus for automatically distinguishing actual oscillometric pulses or Korotkoff sounds from motion induced oscillometric pulses or Korotkoff sounds.

These and other objects of the invention are provided by a system for automatically measuring blood pressure while identifying artifact. The system includes an air pump, valve and pressure transducer pneumatically coupled to a blood pressure cuff. The pressure transducer generates a signal indicative of the air pressure in the blood pressure cuff and a signal corresponding to a blood pressure signal. The system also includes a detector for detecting a QRS complex and a processor connected to the pressure transducer to receive the signal corresponding to the blood pressure signal and connected to the QRS complex detector. The processor also energizes the air pump to inflate the blood pressure cuff, periodically energizes the valve to incrementally reduce the air pressure in the blood pressure cuff, determines whether a single blood pressure signal has been detected between successive QRS complexes in order to identify the blood pressure signal as an actual blood pressure signal, and determines whether multiple blood pressure signals have been detected between successive QRS complexes in order to identify at least some of the blood pressure signals as a motion-induced blood pressure signals. The blood pressure signals may be either oscil lometric pulses or Korotkoff sounds generated in the blood pressure cuff.

BEST MODE FOR CARRYING OUT THE INVENTION

Figure 1:
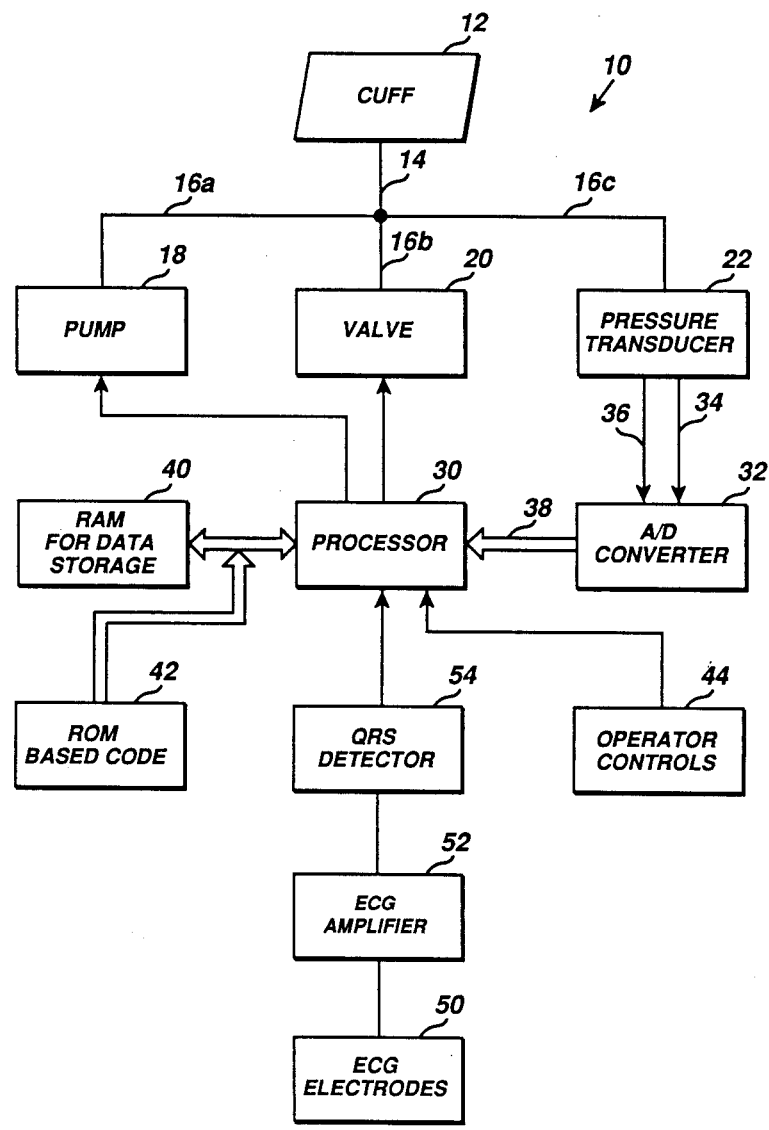
FIG. 1 is a block diagram of a system for automatically making blood pressure measurements with oscillometric techniques using conventional hardware.

One embodiment of a system for identifying artifact in an automatic blood pressure measuring system is illustrated in FIG. 1. The system 10 is composed of a number of hardware components, all of which are conventional. The system includes a conventional blood pressure cuff 12 in fluid communication with conduits 14 and 16, a conventional pump 18, a conventional valve 20, and a conventional pressure transducer 22. The pump 18 and valve 20 are operated by a conventional microprocessor 30.

As explained in greater detail below, during operation of the automatic blood pressure measuring system, the blood pressure cuff 12 is inflated to a pressure that is greater than systolic as indicated by the pressure transducer 22. The valve 20 is then opened, usually for a predetermined period, although it may be continuously open to allow a slight leakage of air from the blood pressure cuff 12. However, the valve 20 normally allows air to escape from the cuff 12 fairly rapidly in relatively small increments. As the pressure in the cuff 12 is reduced, either gradually or incrementally, the pressure in the cuff 12 is measured by the pressure transducer 22.

The pressure in the blood pressure cuff 12 consists of two components, namely, a relatively constant component and a relatively variable component. The relatively constant component is a function of the pressure in the blood pressure cuff 12. The relatively variable component is produced by the minute change in the pressure of the cuff 12 as the blood pressure wave moves through the blood vessels beneath the cuff 12 following each contraction of the heart. Thus, the relatively constant component of the pressure in the cuff 12 can be used as an indication of cuff pressure while the relatively variable component of the pressure in the cuff 12 can be used as an indication of an oscillometric pulse. The pressure transducer 22 therefore generates two output signals; a DC output signal applied to an A/D converter 32 through line 34 and an AC output signal applied to the analog-to-digital converter 32 through line 36. The signal applied through line 34 is thus an indication of cuff pressure while the signal applied through line 36 is produced by the oscillometric pulse. The analog-to-digital converter 32 digitizes the DC and AC signals and outputs digital words indicative of their values through a bus 38 to the microprocessor 30.

As mentioned above, the microprocessor 30 is of conventional variety and, as is typical with such devices, is connected to a random access memory 40 used for temporary storage of data and a read-only memory 42 that contains the software for operating the microprocessor 30. Operator controls 44 such as a keyboard or buttons, are also connected to the microprocessor 30.

The automatic blood pressure measuring system 10 of FIG. 1 also includes an electrocardiograph subsystem including several electrodes 50 attached to the patient in a conventional manner. The electrodes 50 are connected to a conventional ECG amplifier 52 which is, in turn, connected to a conventional QRS detector 54. The QRS detector 54 may be a hardware-based signal processing device. Alternatively, the QRS detector 54 may include an analog-to-digital converter that digitizes the output of the ECG amplifier. The data output by the analog-to-digital converter is then applied to the microprocessor 30. The software controlling the operation of the microprocessor 30 implements an algorithm that is capable of detecting QRS complexes in the digitized ECG signal. Thus, regardless of whether the QRS detector 54 is implemented through hardware or software, the microprocessor 30 receives an indication each time the QRS complex occurs. The QRS complex is a set of three adjacent waveforms, the largest of which is the R-wave. Thus the occurrence of the QRS complex can be determined by detecting only the R-wave utilizing conventional R-wave detector circuits or algorithms. As explained above, the QRS complex is generated once for each heartbeat. Thus, the processor 30 is able to determine the number of heartbeats occurring during a fixed period of time.

Although the measuring system 10 illustrated in FIG. 1 utilizes a pressure transducer 22 outputting separate DC and AC pressure signals, it will be understood that other implementations are possible. For example, the pressure transducer 22 may output a single signal corresponding to both the steady-state and variable pressures in the cuff 12. After this signal is digitized by the analog-to-digital converter 32 and applied to the microprocessor 30, software-based algorithms in the mciroprocessor 30 can detect the steady-state component of the cuff pressure and the variable component variations in the cuff pressure in a manner similar to the manner in which the processor 30 can detect the QRS complex.

Figure 2A:
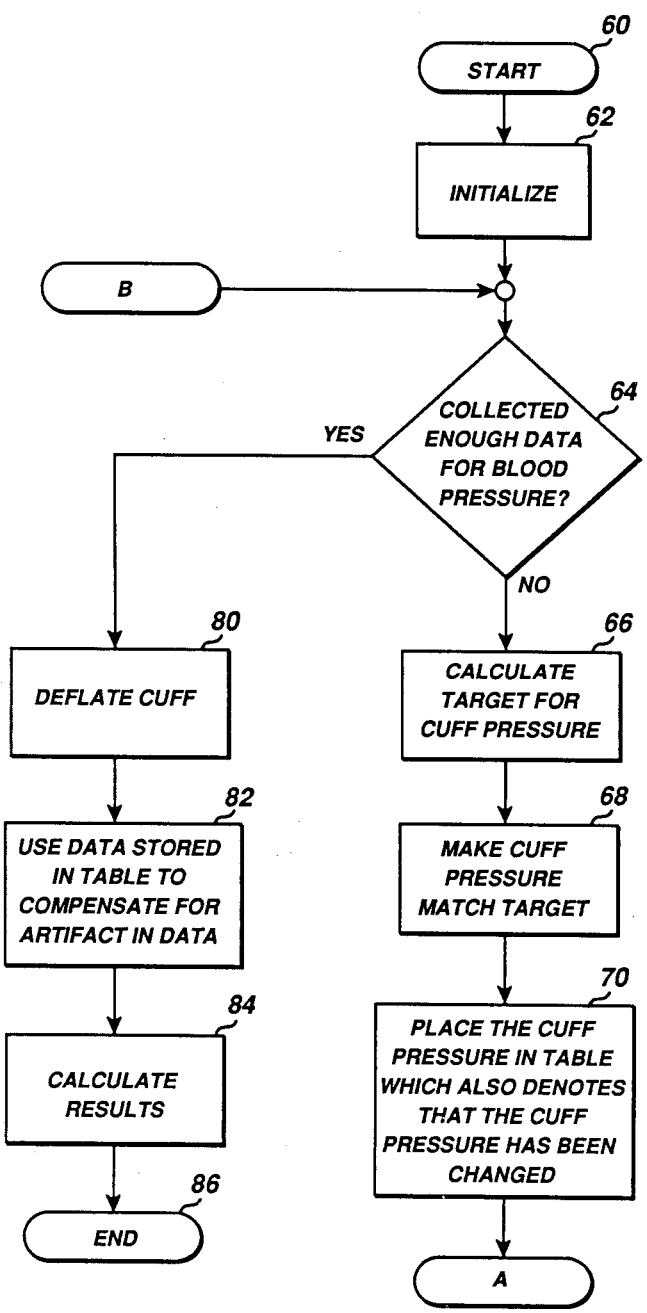
FIG. 2 is a flow chart of software used to program a microprocessor to operate the hardware illustrated in FIG. 1.
Figure 2B:
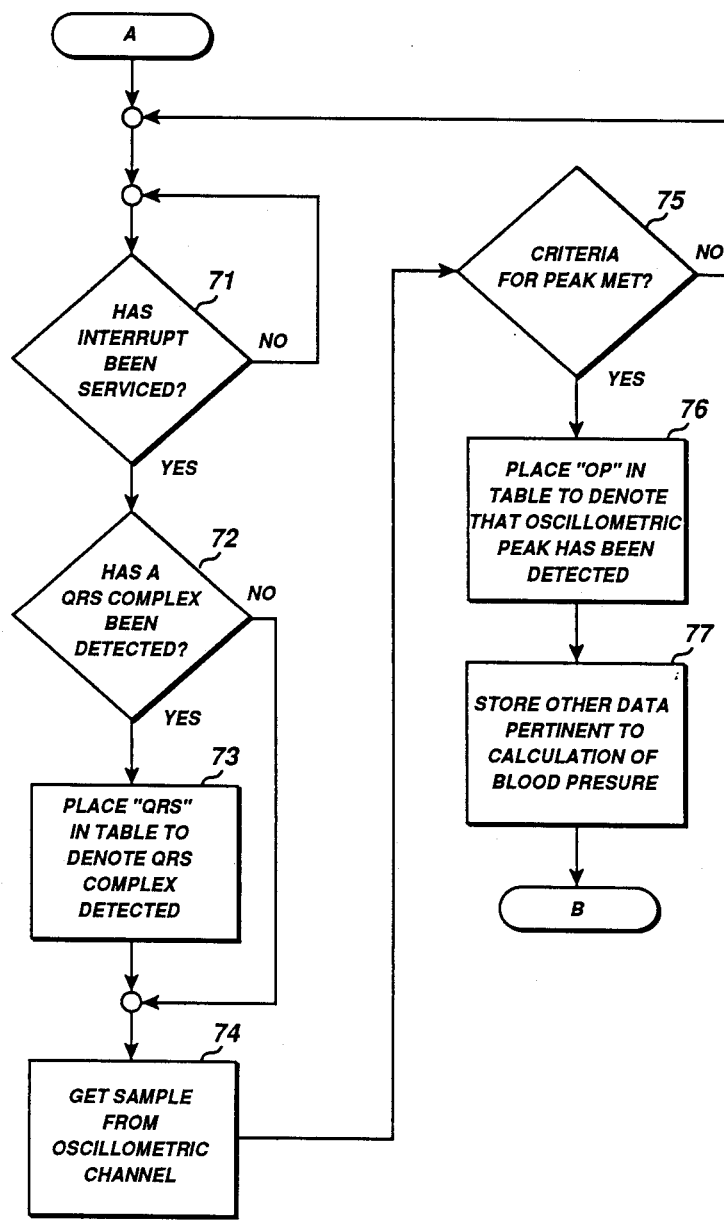

As explained above, the microprocessor 30 is controlled by software that is stored as a series of program instructions in the read-only memory 42. A flow chart from which object code can be easily and quickly written by one skilled in the art to practice the invention is illustrated in FIG. 2. The program starts at 60 either through an operator command, automatically at power-up or when called by another program stored in the read-only memory 42. As is conventional with microprocessor-based systems, the system is initialized at 62 to set up the software for subsequent processing, such as, for example, establishing tables that will subsequently contain data and by setting variables at known values. The program then checks at 64 to determine if enough data has been collected to provide a blood pressure measurement. The decision block 64 is first encountered prior to obtaining any blood pressure data. Thus, when the program initially encounters decision block 64, enough data for a blood pressure determination will not have been collected so that the program will branch to 66 to calculate a target value for the pressure in the blood pressure cuff 12 (FIG. 1). The target pressure for the cuff 12 will, of course, be in excess of the systolic pressure. The microprocessor then energizes the pump 18 (FIG. 1) at 68 while measuring the DC signal output from the pressure transducer 22 and digitized by the analog-to-digital converter 32 until the cuff pressure is equal to the target pressure. On subsequent passes through the steps 66 and 68, the target pressure calculated at 66 will be lower than the initial pressure so that the microprocessor 30 will energize the valve 20 at 68 to reduce the pressure in the cuff 12 to the target pressure. Regardless of whether the pressure in the cuff 12 is being increased to the starting value of incrementally decreased thereafter, the cuff pressure is recorded in a table at 70 so that the data are indicative of detecting the QRS complex and/or an oscillometric pulse can be correlated with the blood pressure and to provide an indication that the blood pressure has been changed.

The microprocessor 30 is interrupt driven in a conventional manner so that it periodically performs an interrupt service routine. The interrupt service routine is clock driven. The main program will loop at 71 as illustrated in FIG. 2 until the interrupt has been serviced. During the interrupt, the digitized DC signal output from the pressure transducer 22 via the A/D converter 32 is read, a sample is obtained from the digitized AC signal output and the output of the QRS detector 54 is checked to determine if a QRS complex has been detected since the last interrupt. After the interrupt has been serviced, the program checks at 72 to determine if a QRS complex had been detected since the previous interrupt. If so, a "QRS" designation is placed in the previously described table at 73 adjacent the digitized value of the cuff pressure recorded in the table.

Regardless of the whether a QRS complex had been detected, the program then samples the digitized AC signal output by the transducer at 74 and establishes the proper criteria for a set of samples being considered an oscillometric pulse and checks to see if those criteria are met at 75. The criteria for determining if a set of samples is characteristic of an oscillometric pulse are conventional and are thus not explained herein. If the samples are not characteristic of an oscillometric pulse, the program returns to 71 to await another interrupt. If the samples do have the characteristics of an oscillometric pulse, the program branches to 76 to place a "OP" designation in the previously described table adjacent any "QRS" designation and the digitized DC signal from the pressure transducer 22 that has been stored in the table to indicate the cuff pressure. Any other data pertinent to the blood pressure calculation are then stored in the table at 77. The program checks to see if enough data had been collected at a given pressure. If enough data have been collected the program then returns to 64 to check if enough data have been collected to determine the patient's blood pressure.

The program will continue to loop through 64-78 until sufficient data have been obtained that the patient's blood pressure can be calculated. The data stored in the table after sufficient data have been obtained at several cuff pressures may appear, for example, as:

140, OP, QRS, OP, 132, QRS, OP, QRS, OP, QRS, 124, QRS, OP, QRS, OP . . .

Note that there are never two "OP's" between "QRS"s. Thus, all of the "OP" designations are considered valid. Note also that the number of oscillometric pulses detected at each pressure may vary. In the event that some of the oscillometric pulses are induced by artifact, the data in the table might be, for example:

140, OP, OP*, QRS, 132, QRS, OP, QRS, OP, 124, OP, QRS, OP, OP*, QRS, OP . . .

Note that the "OP" designations marked with an asterisk are the second "OP" designations between each QRS detection. Insofar as a single oscillometric pulse can occur for each heartbeat, one of these "OP" designations must be a result of artifact.

After sufficient data have been obtained, the program will then branch from 64 to 80, where the microprocessor 30 will continuously actuate the valve 20 to deflate the cuff 12. The program then manipulates the data stored in the table at 82 to compensate for the oscillometric pulses induced by motion artifact. The data resulting from artifact can be compensated for through a variety of conventional means. For example, artifact-induced data can be discarded or they can be replaced by the average of neighboring values. The program then calculates the blood pressure in a conventional manner at 84 and then terminates at 86 until another blood pressure measurement is to be made.

Figure 3A:
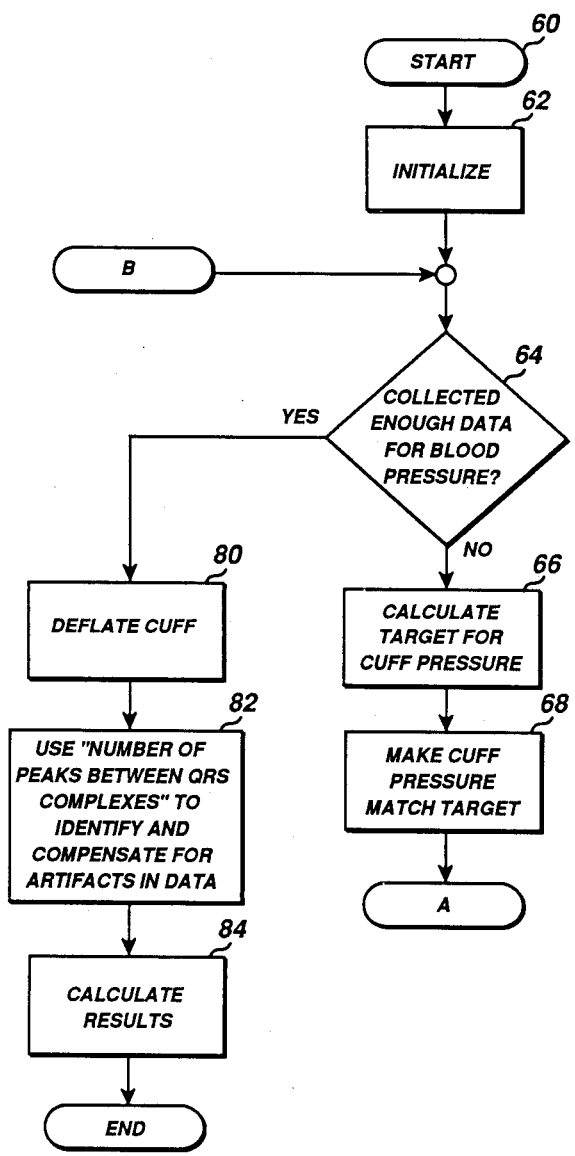
FIG. 3 is a flow chart of an alternative embodiment of software used to program a microprocessor to operate the hardware illustrated in FIG. 1.
Figure 3B:
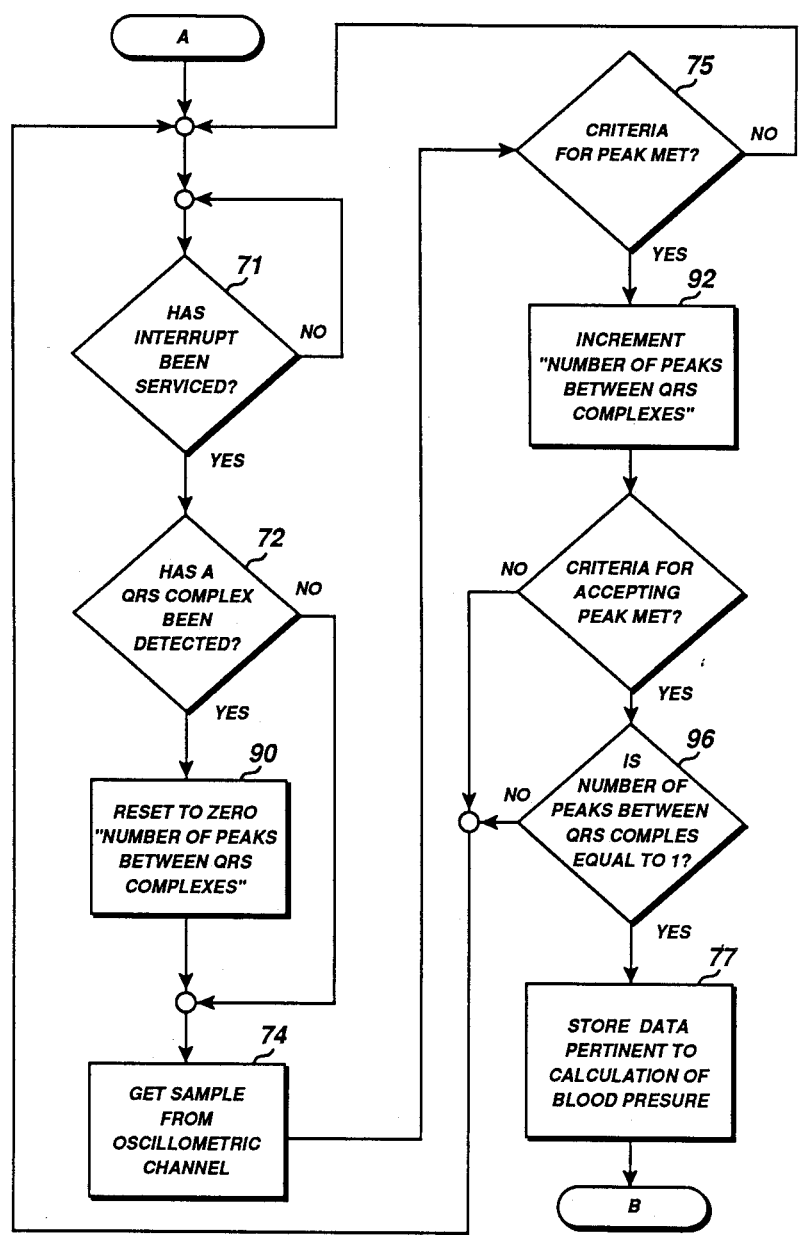

An alternative embodiment of software for controlling the operation of the microprocessor 30 is illustrated in FIG. 3. Most of the software illustrated in FIG. 3 is identical to the software illustrated in FIG. 2. As a result, and in the interest of brevity, this identical software has been provided with corresponding reference numerals and an explanation of such software will not be repeated. The software embodiment illustrated in FIG. 3 differs from the software of FIG. 2 primarily in the manner in which the table of data is organized. More specifically, the software of FIG. 3 does not generate a sequential table of blood pressures, oscillometric peak detections, and QRS complex detections as in the embodiment of FIG. 2. Instead, when a QRS complex is detected at 72, a counter counting the number of oscillometric pulses between QRS complexes is reset at 90. If the criteria established for an oscillometric pulse are subsequently found to exist at 75, the counter recording the number of oscillometric peaks is incremented at 92. In a normal artifact-free environment, the value of the counter at 100 will be equal to 1 since a single oscillometric pulse is detected between QRS complexes and a single QRS complex is detected between oscillometric pulses. If the stored number is not 1, thereby indicating that a previous oscillometric pulse indication is artifact induced, the program returns to 71 to await a subsequent interrupt. If the stored value is equal to 1, thereby indicating that the detected oscillometric pulses are not artifact induced, the program stores the data 77 and then returns to 64 to determine if sufficient data have been collected for a blood pressure measurement. If not, the cuff pressure is changed and the program progresses from 60 through 96, as explained above. If sufficient data have been collected, the program branches through 80-84, as explained above with reference to FIG. 2.

The following is an example of data collected at various cuff pressures. The number of peaks would dictate the decision at 96. If the number were one, the cuff and peak amplitude would be stored at 77.

| CUFF PRESSURE | 140 | 132 | 124 | 124 |
|---|---|---|---|---|
| PEAK AMPLITUDE | 40 | 45 | 60 | 55 |
| NUMBER OF PEAKS | 1 | 1 | 2 | 1 |

In the above example, an artifact occurred at a cuff pressure of 124 since the number "2" indicates that 2 oscillometric pulses were detected between QRS complexes. Therefore, more data were collected at that cuff pressure. This resulted in an amplitude of 55 and the number of peaks equal to 1. At step 77, the good data would overwrite the artifact-induced data.

Although the preferred embodiment utilizes the QRS complex or R-wave to validate the detection of an oscillometric pulse, it will be understood that other arrangements may be used. For example, instead of dectecting oscillometric pulses, the pressure transducer 22 may be used to detect Korotkoff sounds. In this embodiment, the system determines that a Korotkoff sound is not artifact-induced if a single Korotkoff sound is detected between QRS complexes in the same manenr that the system validates an oscillometric pulse by determining that a single oscillometric pulse has occurred between QRS complexes. Similarly, a detected oscillometric pulse can be validated utilizing detected Korotkoff sounds. An oscillometric pulse would be considered not to be artifact-induced if a single oscillometric pulse occurs between two adjacent Korotkoff sounds. Regardless of which technique is used, the system operates by obtaining a blood pressure signal (i.e., oscillometric pulse or Korotkoff sounds) and obtaining a cardio-related signal (i.e., Korotkoff sounds, oscillometric pulses or QRS complex) utilizing two different techniques. The system then ensures that a single blood pressure signal is detected between two adjacent cardio signals. In this manner, the automatic blood pressure measuring system is able to perform accurate measurements in the presence of artifact.

I claim:

1. A system for automatically measuring blood pressure while identifying artifact, comprising:
   a blood pressure cuff;
   an air pump pneumatically coupled to said blood pressure cuff;
   a valve pneumatically coupled to said blood pressure cuff;
   a pressure transducer pneumatically coupled to said blood pressure cuff, said pressure transducer generating a signal indicative of the air pressure in said blood pressure cuff and a signal corresponding to a blood pressure signal;
   ECG sensing means for detecting a QRS complex and for generating an output signal responsive to detecting a QRS complex; and
   processor means connected to said pressure transducer to receive said signal corresponding to said blood pressure signal and connected to said ECG sensing means to detect said output signal, said processor means for energizing said air pump to inflate said blood pressure cuff, periodically energizing said valve to incrementally reduce the air pressure in said blood pressure cuff, determining whether a single blood pressure signal has been detected between successive QRS complexes in order to identify said blood pressure signal as an actual blood pressure signal, and determining whether multiple blood pressure signals have been detected between successive QRS complexes in order to identify at least some of said blood pressure signals as motion-induced blood pressure signals.

2. The automatic blood pressure measuring system of claim 1 wherein said blood pressure signals are oscillometric pulses generated in said blood pressure cuff.

3. The automatic blood pressure measuring system of claim 1 wherein said blood pressure signals are Korotkoff sounds generated in said blood pressure cuff.

4. The automatic blood pressure measuring system of claim 1 wherein said processing means sequentially records the cuff pressure for each value of pressure in said blood pressure cuff and, for each cuff pressure recording, records the detection of a blood pressure signal and the detection of a QRS complex in chronological order, said processor means further determining if a single blood pressure signal is recorded between two successively detected QRS complexes, thereby indicating that said blood pressure signal is an actual blood pressure signal, and determining if multiple detected blood pressure signals are recorded between two successively detected QRS complexes, thereby indicating that at least some of said blood pressure signals are motion induced blood pressure signals.

5. The automatic blood pressure measuring system of claim 1 wherein said processing means sequentially records the cuff pressure for each value of pressure in said blood pressure cuff, and wherein said processing means forms a table and, for each value of pressure in said blood pressure cuff, records in said table the cuff pressure and the number of blood pressure signals detected between successive detections of a QRS complex, said processing means further determining if the number recorded in said table as the number of blood pressure signals detected between successive detections of a QRS complex is one, thereby indicating that said blood pressure signal is an actual blood pressure signal, or if the number recorded in said table as the number of blood pressure signals detected between successive detections of a QRS complex is greater than one, thereby indicating that at least some of said blood pressure signals are motion-induced blood pressure signals.

* * * * *